(12) United States Patent
Kothari et al.

(10) Patent No.: US 12,121,741 B2
(45) Date of Patent: Oct. 22, 2024

(54) EXTRAORAL MASK FOR THE TREATMENT OF ORAL MUCOSITIS

(71) Applicant: MUREVA PHOTOTHERAPY, INC., Strongsville, OH (US)

(72) Inventors: Vedang Kothari, Cleveland, OH (US); Jason D. Lazzara, Cleveland, OH (US); Jordan W. Oja, Cleveland, OH (US); Samuel J. Shelnutt, Olmsted Township, OH (US)

(73) Assignee: MUREVA PHOTOTHERAPY, INC., Strongsville, OH (US)

( * ) Notice: Subject to any disclaimer, the term of this patent is extended or adjusted under 35 U.S.C. 154(b) by 926 days.

(21) Appl. No.: 17/051,283

(22) PCT Filed: May 16, 2019

(86) PCT No.: PCT/US2019/032648
§ 371 (c)(1),
(2) Date: Oct. 28, 2020

(87) PCT Pub. No.: WO2019/222492
PCT Pub. Date: Nov. 21, 2019

(65) Prior Publication Data
US 2021/0228900 A1 Jul. 29, 2021

Related U.S. Application Data

(60) Provisional application No. 62/672,077, filed on May 16, 2018.

(51) Int. Cl.
*A61H 21/00* (2006.01)
*A61N 5/06* (2006.01)
(Continued)

(52) U.S. Cl.
CPC ............ *A61N 5/0603* (2013.01); *A61H 21/00* (2013.01); *A61N 5/0613* (2013.01); *A61B 1/24* (2013.01);
(Continued)

(58) Field of Classification Search
CPC ................ A61N 5/0603; A61N 5/0613; A61N 2005/0606; A61N 2005/0628;
(Continued)

(56) References Cited

U.S. PATENT DOCUMENTS

2007/0208395 A1 9/2007 Leclerc et al.
2007/0219605 A1* 9/2007 Yaroslavsky ........ A61N 5/0613
607/88
(Continued)

FOREIGN PATENT DOCUMENTS

WO 2004/043543 5/2004
WO 2017/044931 3/2017
WO WO-2018213893 A1 * 11/2018 ............... A61N 5/06

OTHER PUBLICATIONS

International Search Report and Written Opinion for corresponding International Patent No. PCT/US2019/032648 mailed on Jul. 16, 2019.

*Primary Examiner* — Ankit D Tejani
*Assistant Examiner* — Joshua Brendon Solomon
(74) *Attorney, Agent, or Firm* — Renner, Otto, Boisselle & Sklar, LLP

(57) ABSTRACT

A phototherapy device for modulating an optical dosage delivered to targeted tissues extraorally based on measured tissue properties, such that the targeted tissues receive a particular dose of optical power.

29 Claims, 6 Drawing Sheets

(51) Int. Cl.
*A61B 1/24* (2006.01)
*A61B 5/00* (2006.01)
*A61B 5/055* (2006.01)
*A61B 8/12* (2006.01)

(52) U.S. Cl.
CPC ........... *A61B 5/0066* (2013.01); *A61B 5/0086* (2013.01); *A61B 5/055* (2013.01); *A61B 8/12* (2013.01); *A61H 2201/10* (2013.01); *A61N 2005/0606* (2013.01); *A61N 2005/0628* (2013.01); *A61N 2005/0647* (2013.01); *A61N 2005/0652* (2013.01); *A61N 2005/066* (2013.01); *A61N 2005/0663* (2013.01)

(58) Field of Classification Search
CPC .... A61N 2005/0647; A61N 2005/0652; A61N 2005/066; A61N 2005/0663; A61N 2005/0627; A61N 2005/0659; A61H 21/00; A61H 2201/10; A61B 1/24; A61B 5/0066; A61B 5/0086; A61B 5/055; A61B 8/12

See application file for complete search history.

(56) References Cited

U.S. PATENT DOCUMENTS

| | | | |
|---|---|---|---|
| 2009/0287195 A1* | 11/2009 | Altshuler | A46B 15/0036 606/9 |
| 2012/0148975 A1 | 6/2012 | Brawn | |
| 2012/0148976 A1* | 6/2012 | Brawn | A61N 5/0613 433/29 |
| 2017/0164848 A1* | 6/2017 | Nadeau | A61B 5/14552 |
| 2017/0173354 A1* | 6/2017 | Demarest | A61N 5/0613 |
| 2018/0093106 A1* | 4/2018 | Binner | A61K 47/46 |
| 2018/0099143 A1 | 4/2018 | Kim et al. | |
| 2020/0101311 A1* | 4/2020 | Tahghighi Jafarzadeh | A61N 5/0613 |

* cited by examiner

200

Irradiate target regions of a users oral cavity with light prior to symptoms of oral mucositis symptoms being present 202

EXTRAORAL MASK FOR THE TREATMENT OF ORAL MUCOSITIS

RELATED APPLICATIONS

This application is a national phase of International Application No. PCT/US2019/032648 filed May 16, 2019 which claims the benefit of U.S. Application No. 62/672,077 filed on May 16, 2018 that is herein incorporated by reference in its entirety.

TECHNICAL FIELD

The present disclosure relates generally to phototherapy and, in particular, to devices for applying phototherapy to tissue associated with the oral cavity.

BACKGROUND

Phototherapy can be utilized for treating and providing pain relief for various conditions, including a condition called Oral Mucositis (OM). Phototherapy can be delivered in several ways, e.g., directly to the tissue via Low Level Laser Therapy (LLLT) or via a light emitting diode (LED) array that propagates light through the skin into the affected region.

The problem with the current LLLT approach is the cost of the laser and the labor intensiveness of the procedure. Furthermore, the interoperator variability reduces the accuracy of phototherapy delivered to the patient. Additionally, the patient must hold their mouth open for a prolonged period of time, which is uncomfortable and may be extremely painful as the condition progresses.

Alternatively, the complications with the current extra-oral LED array approach is that the LEDs are housed in a portable 'lamp' that must be held a fixed distance from the skin and operated by a trained technician. The LED 'lamp' must be moved to the various locations of the cheeks and neck to deliver the appropriate dosage of light therapy to the affected tissues. Due to varying tissue thickness and optical properties, each location requires a different light intensity to deliver the phototherapy deep into the tissues. Furthermore, the extra-oral approach does not target the inner oral organs such as the tonsils and uvula.

SUMMARY

The present disclosure provides a phototherapy device for modulating an optical dosage delivered to targeted tissues extraorally based on measured tissue properties, such that the targeted tissues receive a particular dose of optical power.

According to one aspect, there is provided a phototherapy device for modulating an optical dosage delivered to tissues based on an output from a tissue sensor. The phototherapy device includes a mask shaped to conform to an anatomical location when placed against the anatomical location. The phototherapy device also includes an illumination source comprising an array of light sources configured to emit light to illuminate target regions when the mask is placed against the anatomical location. The phototherapy device further includes circuitry configured to: receive from the tissue sensor tissue properties. The received tissue properties affect delivery of light to the target regions. The circuitry is also configured to, based on the received tissue properties, modulate a property of light emitted by the array of light sources and directed towards the target regions, such that the targeted regions each receive a particular dose of optical power.

Alternatively or additionally, the property of light includes at least one of: an intensity, a wavelength, a duration of emission, a coherence, time modulation of emission, or a distance of emission from the target regions.

Alternatively or additionally, when the tissue properties indicate increased attenuation of light prior to reaching the target regions compared to a threshold, the circuitry is configured to affect the light emitted by the array of light sources in the target regions by at least one of: decreasing an intensity, decreasing a coherence, decreasing a wavelength, decreasing a duration of emission, altering a time modulation of the emission such that total emission time is decreased, or increasing a distance of emission from the target regions. When the tissue properties indicate decreased attenuation of light prior to reaching the target regions compared to the threshold, the circuitry is configured to affect the light emitted by the array of light sources in the target regions by at least one of: increasing the intensity, increasing the coherence, increasing the wavelength, increasing the duration of emission, altering a time modulation of the emission such that the total emission time is increased, or decreasing the distance of emission from the target regions.

Alternatively or additionally, when the distance to the target regions received from the tissue sensor is below a minimum distance threshold, the circuitry is configured to affect the light emitted by the array of light sources in the target regions by at least one of: decreasing the intensity, decreasing the coherence, decreasing the wavelength, decreasing the duration of emission, or altering the time modulation of the emission such that total emission time is decreased. When the distance to the target regions received from the tissue sensor is above a maximum distance threshold, the circuitry is configured to affect the light emitted by the array of light sources in the target regions by at least one of: increasing the intensity, increasing the coherence, increasing the wavelength, decreasing the duration of emission, or altering the time modulation of the emission such that total emission time is increased.

Alternatively or additionally, the particular dose of optical power varies between at least two of the target regions.

Alternatively or additionally, the particular dose of optical power for each of the target regions is between 10 milliwatts/cm2 and 150 milliwatts/cm2.

Alternatively or additionally, the particular dose of optical power received by each of the target regions does not vary between the target regions by more than 20%.

Alternatively or additionally, the target regions include at least one of: a tonsillar region, buccal tissues of an oral cavity, a hard palate, or a soft palate.

Alternatively or additionally, the phototherapy device also includes the tissue sensor configured to detect the tissue properties.

Alternatively or additionally, the tissue sensor detects at least one of a skin pigment, a tissue thickness, or a tissue fluid content.

Alternatively or additionally, the tissue sensor comprises at least one of a magnetic resonance imager (MRI), an infrared (IR) sensor, an ultrasound sensor, an OCT sensor, a dielectric sensor, a photodiode, or a camera.

Alternatively or additionally, the phototherapy device further includes an intraoral component having a contour complimentary to a palate of a user.

Alternatively or additionally, the tissue sensor is located on the intraoral component and the detected tissue properties include a distance to the target regions.

Alternatively or additionally, the tissue sensor is located on the intraoral component. The detected tissue properties include a location of the target regions.

The circuitry is configured to control the regions illuminated by the illumination source, such that the target regions are preferentially illuminated by the illumination source.

Alternatively or additionally, the target regions are preferentially illuminated by the illumination source such that an optical power of light received by the target regions is at least five times higher than an optical power of light received by non-target regions.

Alternatively or additionally, the array of light sources comprises a plurality of light emitting diodes (LEDs).

Alternatively or additionally, the array of light sources additionally includes one or more lasers.

Alternatively or additionally, the array of light sources is located on the mask.

Alternatively or additionally, the array of light sources is positioned on the mask such that heat generated by the array of light sources is directed away from the anatomical location when the mask is positioned against the anatomical location.

Alternatively or additionally, the phototherapy device also includes one or more temperature sensors positioned to detect a temperature of a contacting surface of the mask. The contacting surface contacts the anatomical location when the mask is positioned against the anatomical location. The circuitry is further configured to receive a temperature reading from the one or more temperature sensors and reduce the emission of light from the array of light sources when the received temperature reading exceeds a temperature threshold.

Alternatively or additionally, the mask includes a gel positioned between the array of light sources and a contacting surface of the mask. The contacting surface contacts the anatomical location when the mask is positioned against the anatomical location.

Alternatively or additionally, the gel is a thermal insulator configured to reduce a transfer of heat generated by the illumination source to the contacting surface.

Alternatively or additionally, the phototherapy device further includes an actuator configured to alter tissue properties to improve penetration to the targeted regions of the light emitted by the illumination source.

Alternatively or additionally, the actuator emits at least one of vibrations or sound waves.

Alternatively or additionally, the phototherapy device further includes one or more safety sensors configured to detect when the mask is positioned adjacent the anatomical location. The circuitry is further configured to: (1) receive from the one or more safety sensors a signal indicating whether the mask is positioned adjacent the anatomical location; and when the signal indicates that the mask is not positioned adjacent the anatomical location, the circuitry prevents the illumination source from emitting light.

Alternatively or additionally, the phototherapy device further includes a battery configured to provide electrical power to at least one the illumination source or the circuitry.

Alternatively or additionally, the anatomical location includes at least one of a mouth or a neck.

Alternatively or additionally, the mask has a softness less than or equal to 50 Shore A durometer.

Alternatively or additionally, a wavelength of light emitted by the illumination source is from 600 nm to 1000 nm.

The present disclosure also provides an intraoral phototherapy device for directing light onto an oral cavity of a patient, the intraoral phototherapy device includes a main body shaped to conform to contours of the oral cavity when inserted therein. The main body includes a pair of laterally spaced side wings sized and shaped to be received between a patient's teeth and cheeks on opposite sides of the oral cavity. The main body also includes an illumination source comprising a plurality of micro-light emitting diodes (LEDs) positioned on the main body such that light emitted by the micro-LEDs is directed to targeted regions of the oral cavity when the main body is positioned in the oral cavity. The targeted regions of the oral cavity include the mandibular and maxillary buccal surfaces.

Alternatively or additionally, the main body additionally includes a central protrusion intermediate the side wings that directs the light to particular targeted regions of the oral cavity. The particular targeted regions of the oral cavity additionally include at least one of a tongue, tonsils, and palate.

Alternatively or additionally, the intraoral phototherapy device further including a battery configured to supply electrical power to the illumination source.

The present disclosure also provides a method of preventing oral mucositis. The method includes, prior to symptoms of oral mucositis being present, irradiating target regions of a user's oral cavity with light. The target regions include at least one of buccal tissues, tongue tissues, palate tissues, or tonsillar tissues.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

DETAILED DESCRIPTION

Figure 1:
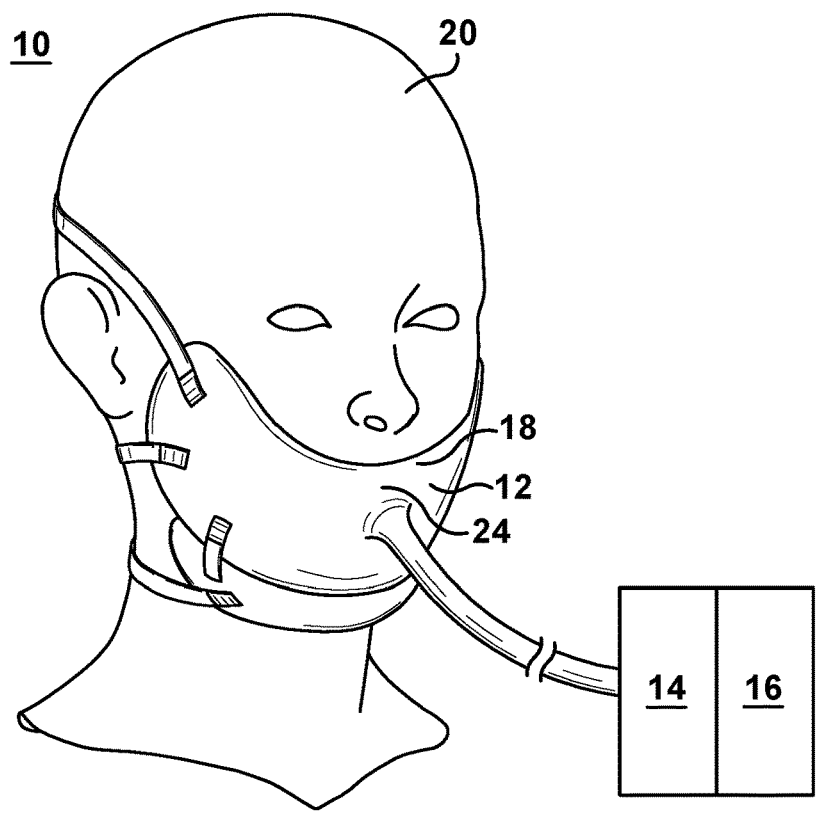
FIG. 1 is a schematic diagram of an exemplary embodiment of a phototherapy device positioned on a patient.

The present invention is now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

The present invention provides a phototherapy device including a mask, an illumination, and circuitry. The circuitry is configured to receive tissue properties from a sensor and, based on the received tissue properties, modulate a property of light (1) emitted by the array of light sources and (2) directed towards the target regions, such that the targeted tissues each receive a particular dose of optical power.

Turning to FIG. 1, an exemplary phototherapy device 10 for modulating an optical dosage delivered to tissues based on an output from a tissue sensor is shown. The phototherapy device includes a mask 12, an illumination source 14, and circuitry 16. The phototherapy device 10 may also include the tissue sensor 30 configured to detect the tissue properties. The illumination source 14 includes an array of light sources 22 configured to emit light 28 to illuminate target regions 24 when the mask 10 is placed against an anatomical location 18. The circuitry 16 is configured to receive tissue properties and, based on the received tissue properties, modulate a property of light 28 emitted by the illumination source 14, such that targeted tissues 24 each receive a particular dose of optical power.

Figure 11:
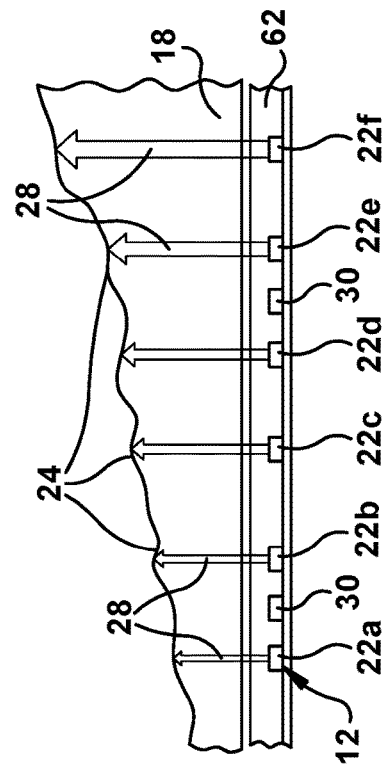
FIG. 11 is a zoomed in schematic diagram showing relative light paths, light sources, and sensors.

Turning to FIGS. 3-8, the illumination source 14 includes an array of light sources 22 configured to emit light 28 to illuminate the target regions 22 when the mask 12 is placed against the anatomical location 22. The array of light sources 22 may be located on the mask 12. The array of light sources 22 may be positioned on the mask 12, such that heat generated by the array of light sources 22 is directed away from the anatomical location 18 when the mask is positioned against the anatomical location. For example, as shown in FIG. 11, the array of light sources 22 may be located adjacent a surface of the mask 12 opposite a skin surface of the user when the mask is positioned against the anatomical location 22. The array of light sources 22 may be spaced to control light uniformity when illuminating a target region 24.

The array of light sources 22 may include a plurality of light emitting diodes (LEDs). The array of light sources 22 may additionally include one or more lasers. As will be understood by one of ordinary skill in the art, the array of light sources 22 may include any suitable source of electromagnetic radiation. The array of light sources 22 may emit light 28 having a wavelength from 600 nm to 1000 nm. For example, the light source may emit electromagnetic radiation having a wavelength approximately equal to at least one of 630 nm, 660 nm, 670 nm, 810 nm, or 880 nm.

As shown in FIGS. 3-8, the position and number of light sources 22 and sensors 30 may vary. The position and number of light sources 22 may be chosen depending on the target regions being treated and based on properties of the user (e.g., size, weight, skin tone, etc.).

Figure 2:
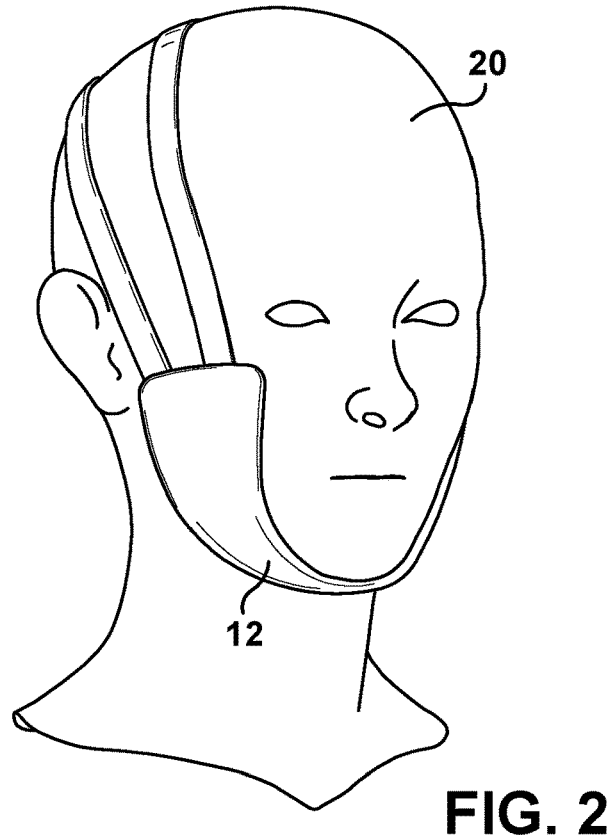
FIG. 2 is a schematic diagram of an alternative exemplary embodiment of a phototherapy device positioned on the patient.
Figure 3:
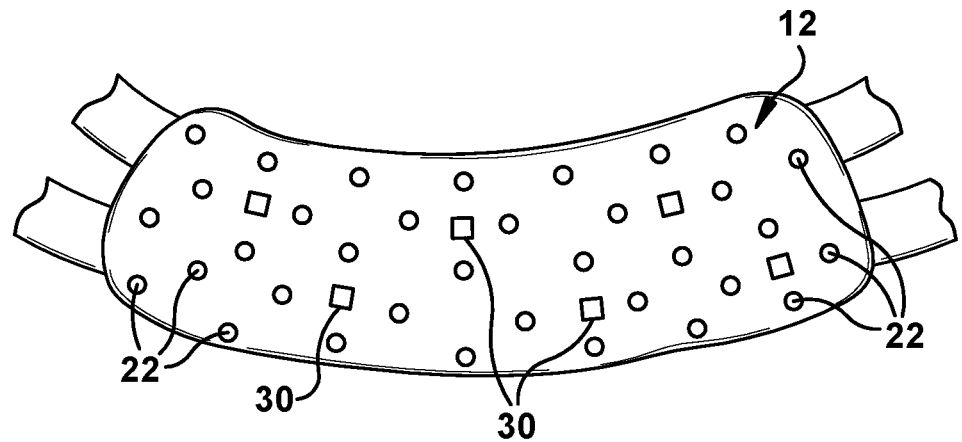
FIG. 3 is a schematic diagram of an exemplary embodiment of the phototherapy device showing sensors and multiple light sources.
Figure 4:
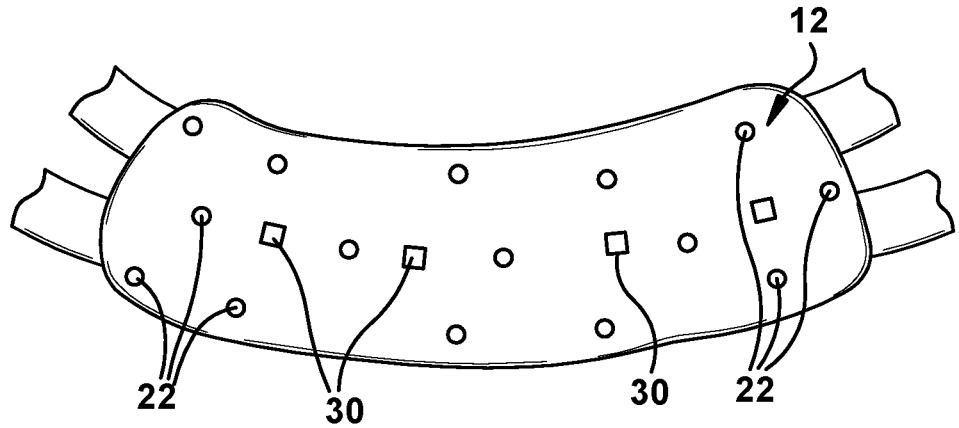
FIG. 4 is a schematic diagram of the exemplary embodiment of the phototherapy device with a lower density of sensors and multiple light sources than the phototherapy device of FIG. 3.
Figure 5:
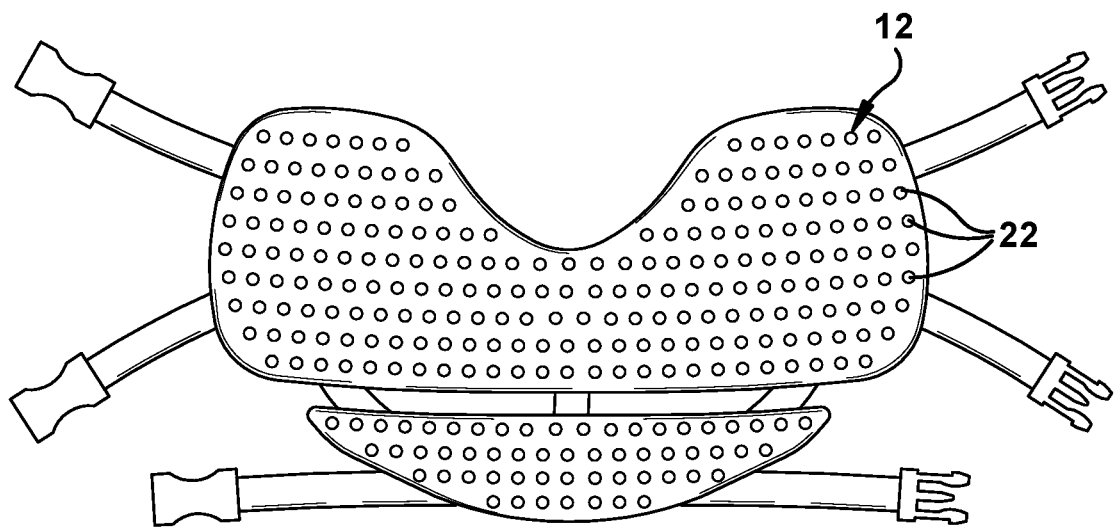
FIG. 5 is a schematic diagram of a phototherapy device with two separate connected portions.
Figure 6:
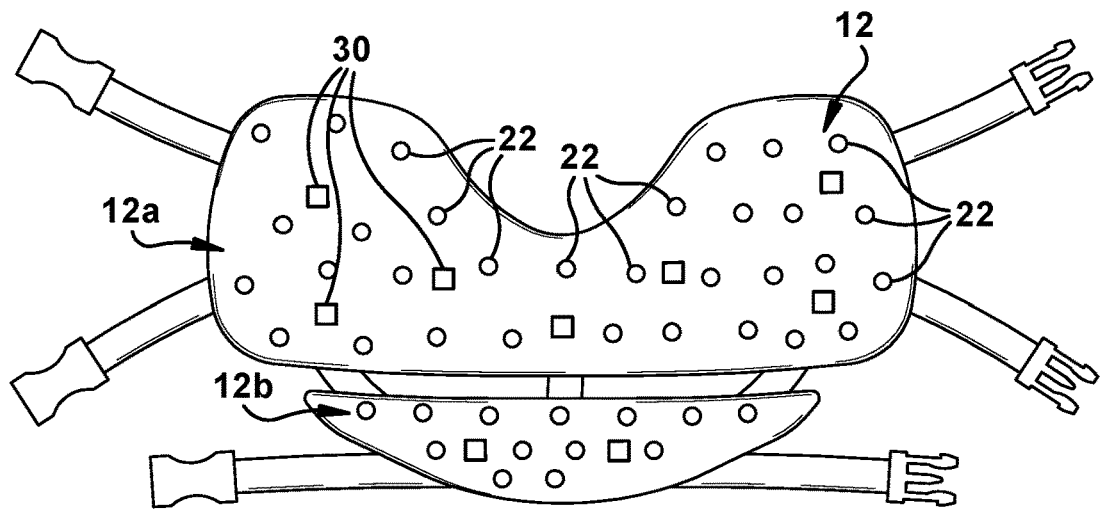
FIGS. 6-8 are schematic diagrams of the phototherapy device of FIG. 5 showing different numbers of light sources and sensors.
Figure 7:
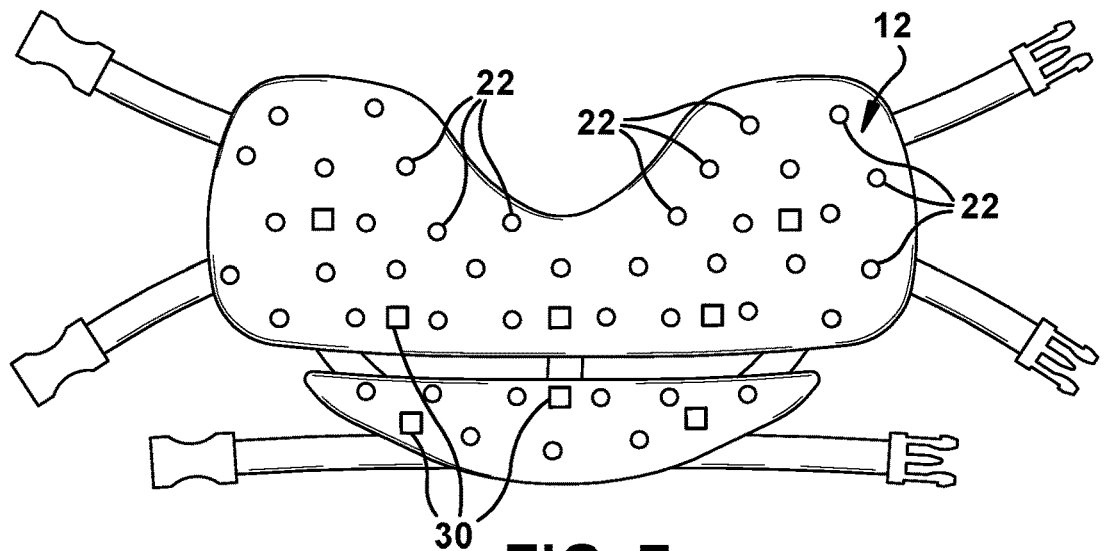
Figure 8:
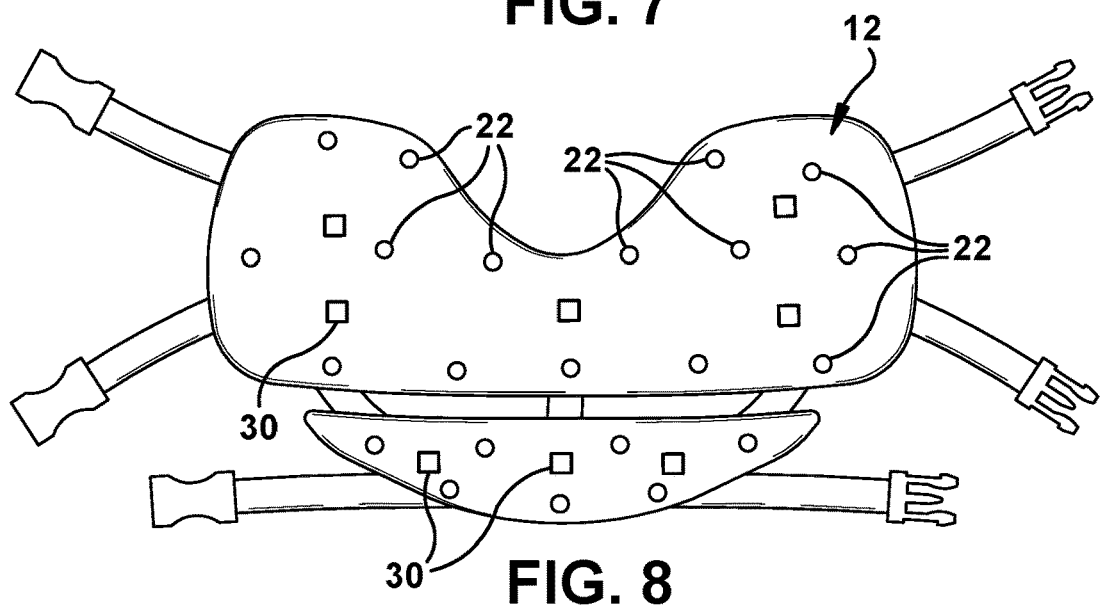

The mask 12 is shaped to conform to an anatomical location 18 when placed against the anatomical location 18. For example, in FIG. 1, the anatomical location 18 may comprise a lower portion of a face of a patient 20 including the mouth (e.g., including the area around the mouth, cheeks, and a neck of the patient 20). In the embodiment shown in FIG. 2, the anatomical location includes the area under the chin. By placing light sources 22 in the area under the patient's chin, light may be delivered to, e.g., the tonsillar region and/or oral cavity.

The mask may be made of any suitable material. For example, the mask may comprise a rubber, plastic, or any suitable material for positioning the illumination source 14 relative to the anatomical location 18. As an example, the example may be made of a material having a softness less than or equal to 50 Shore A durometer. For example, the mask 12 may be relatively malleable such that the mask 12 conforms to the shape of the anatomical location 18 when the mask 12 is pressed against the anatomical location 18. Alternatively, the mask 12 may be more rigid and have a shape complementary to that of the anatomical location 18 even when the mask 12 is not being pressed against the anatomical location 18.

The mask 12 may also be formed of a material suitable to be surface disinfected using standard techniques (e.g., chemical disinfection using alcohol).

As shown in FIGS. 1 and 5-8, the mask 12 may include an upper portion 12a shaped to be positioned adjacent a jaw and mouth; and a lower portion 12b shaped to be positioned adjacent a neck. The upper and lower portion may be electrically and/or optically connected or independent from one another.

The mask 12 may be held in place relative to the anatomical location 18 using straps (FIGS. 1-8), adhesive, or using any suitable means. Alternatively or additionally, the mask 12 may be handheld by a user to maintain a position of the mask 12 relative to the anatomical location 18.

The circuitry 16 is configured to receive, from the tissue sensor 30, tissue properties. The received tissue properties affect delivery of light 28 to the target regions. For example, the tissue properties may comprise attenuation of light 28 prior to reaching the target regions, such as tissue pigmentation, tissue density, fluid content, distance from tissues, etc. Based on the received tissue properties, the circuitry 16 is configured to modulate a property of light 28 emitted by the array of light sources 22 and directed towards the target regions 24, such that the targeted regions each receive a particular dose of optical power.

The property of light 28 altered by the circuitry 16 may include at least one of: an intensity, a wavelength, a duration of emission, a coherence, time modulation of emission, or a distance of emission from the target regions. For example, when the tissue properties indicate increased attenuation of light 28 prior to reaching the target regions 24 compared to a threshold, the circuitry 16 may be configured to affect the light 28 emitted by the array of light sources 22 in the target regions by at least one of: decreasing an intensity, decreasing a coherence, decreasing a wavelength, decreasing a duration of emission, altering a time modulation of the emission such that total emission time is decreased, or increasing a distance of emission from the target regions. In this way, the circuitry 16 may alter the properties of the light 28 emitted by the illumination source 16 to compensate for increased attenuation of light 28 prior to the light 28 reaching the target regions 24 to ensure that enough light 28 reaches the target regions 24.

Similarly, when the tissue properties indicate decreased attenuation of light 28 prior to reaching the target regions 24 compared to the threshold, the circuitry 16 may be configured to affect the light 28 emitted by the array of light sources 22 in the target regions 24 by at least one of: increasing the intensity, increasing the coherence, increasing the wavelength, increasing the duration of emission, altering a time modulation of the emission such that the total emission time is increased, or decreasing the distance of emission from the target regions. In this way, the circuitry 16 may alter the properties of the light 28 emitted by the illumination source 16 to compensate for decreased attenuation of light 28 prior to the light 28 reaching the target regions 24 to ensure that too much light 28 does not reach the target regions 24.

Figure 10:
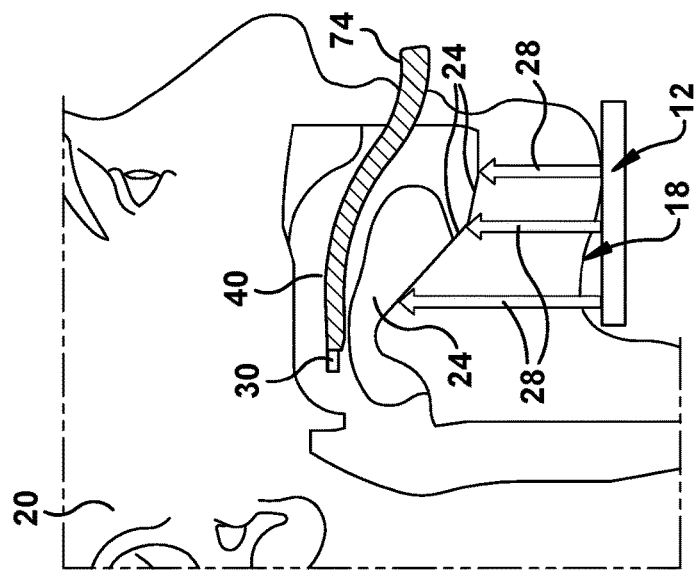
FIG. 10 is a schematic diagram showing relative light paths through the neck.
Figure 9:
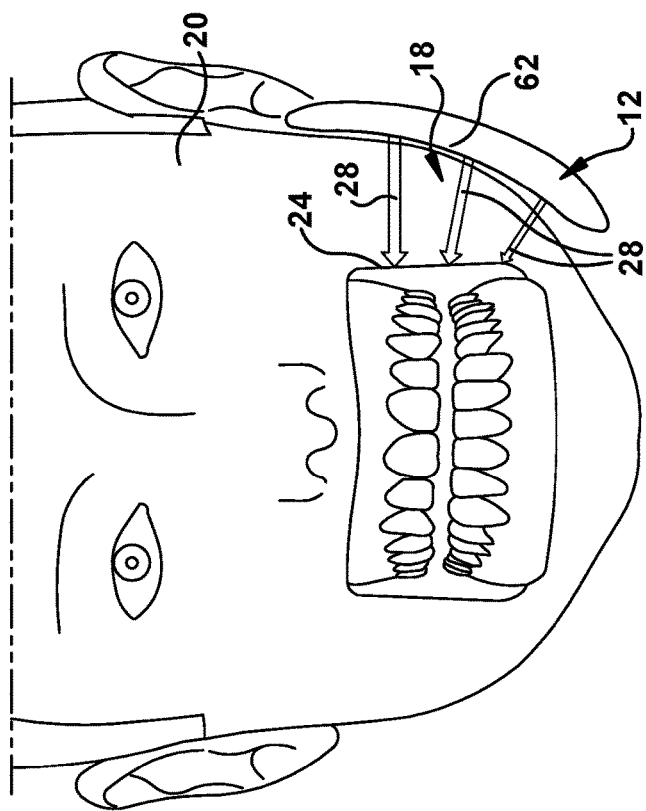
FIG. 9 is a schematic diagram showing relative light paths through the cheek.

In another example shown in FIGS. 9-11, when the distance to the target regions 24 received from the tissue sensor 30 is below a minimum distance threshold, the circuitry 16 may be configured to affect the light 28 emitted by the array of light sources 22 in the target regions 22 by at least one of: decreasing the intensity, decreasing the coherence, decreasing the wavelength, decreasing the duration of emission, or altering the time modulation of the emission such that total emission time is decreased.

In this example, when the distance to the target regions 24 received from the tissue sensor is above a maximum distance threshold, the circuitry 16 may be configured to affect the light 28 emitted by the array of light sources 22 in the target regions 24 by at least one of: increasing the intensity, increasing the coherence, increasing the wavelength, decreasing the duration of emission, or altering the time modulation of the emission such that total emission time is increased.

For example, turning to FIG. 11, light sources 22a and 22b are located closer to the target regions 24 than light sources 22c-22f. Consequently, the controller 16 may decrease the intensity of light 28 emitted by light sources 22a and 22b relative to light sources 22c-22f.

As another example, the illumination source 14 supplying the light 28 may have various light output intensity settings. Each setting may be associated with a particular distance to a nearest tissue. For a given light output intensity setting, if the nearest tissue is closer (as detected by the sensor 30) than the distance associated with the setting, then the setting may be changed to a setting having a lower light output intensity. Conversely, if the nearest tissue is farther away than the distance associated with the setting, then the setting may be changed to a setting having a higher light output intensity. The circuitry 16 may monitor the output of the illumination source 14 (e.g., using the tissue sensor) to detect changes in distance to a nearest tissue (e.g., by continuously or periodically receiving an output from the tissue sensor). When the output of the tissue sensor changes, the circuitry 16 may change the setting of the illumination source 14 to match the distance output by the tissue sensor. In this way, the circuitry 16 may control the light output intensity based on the distance to the nearest tissue (as detected by the tissue sensor).

The particular dose of optical power delivered to the target regions 24 may vary between at least two of the target regions. For example, the target regions 24 may include at least one of: a tonsillar region, buccal tissues of an oral cavity, a hard palate, a soft palate, or the tongue. The particular dose of optical power delivered to the different tissues may be varied based on known effective optical doses for treating different issues. For example, the particular dose for the tonsillar region may be different from the particular dose of optical power delivered to the hard palate.

The particular dose of optical power for each of the target regions may be between 10 milliwatts/cm2 and 150 milliwatts/cm2. The particular dose of optical power received by each of the target regions may not vary between the target regions by more than 20%.

As will be understood by one of ordinary skill in the art, the circuitry 16 may have various implementations. For example, the circuitry 16 may include any suitable device, such as a processor (e.g., CPU), programmable circuit, integrated circuit, memory and I/O circuits, an application specific integrated circuit, microcontroller, complex programmable logic device, other programmable circuits, or the like. The circuitry 16 may also include a non-transitory computer readable medium, such as random access memory (RAM), a read-only memory (ROM), an erasable programmable read-only memory (EPROM or Flash memory), or any other suitable medium. Instructions for performing the method described below may be stored in the non-transitory computer readable medium and executed by the circuitry 16. The circuitry 16 may be communicatively coupled to the computer readable medium and a network interface through a system bus, mother board, or using any other suitable structure known in the art. The circuitry 16 may receive parameters for controlling the illumination source 14 via the network interface. Alternatively or additionally, the circuitry 16 may receive particular optical doses for different tissues from the network interface and the circuitry 16 may control the illumination source 14 so that the received optical doses are received by the respective tissues.

As described above, the phototherapy device 10 may additionally include the tissue sensor 30. The tissue sensor 30 may comprise any suitable device for measuring tissue properties that affect transmission and attenuation of light 28. For example, the tissue sensor 30 may detect at least one of a skin pigment, a tissue thickness, or a tissue fluid content. The tissue sensor 30 may comprise at least one of a magnetic resonance imager (MRI), an infrared (IR) sensor, an ultrasound sensor, an OCT sensor, a dielectric sensor, a photodiode, or a camera.

The measuring of the tissue properties by the tissue sensor 30 may occur while the illumination source 12 is illuminating the target regions 24. Alternatively or additionally, the tissue sensor 30 may measure the tissue properties prior to illumination of the target regions 24. For example, an MRI may be performed of the target regions prior to illuminating the target regions 24 with the phototherapy device 10. In this way, the intraoral tissue may be mapped in advanced and the mapping may be received by the circuitry 16. The circuitry 16 may then use this mapping to modulate the light emitted by the illumination source 14.

Figure 14:
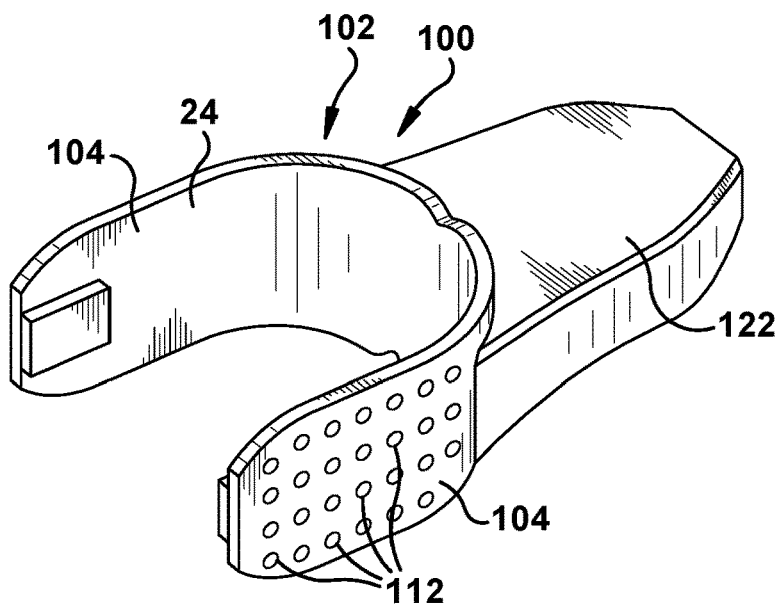
FIG. 14 is a schematic diagram of an intraoral phototherapy device.
Figures 15, 16:
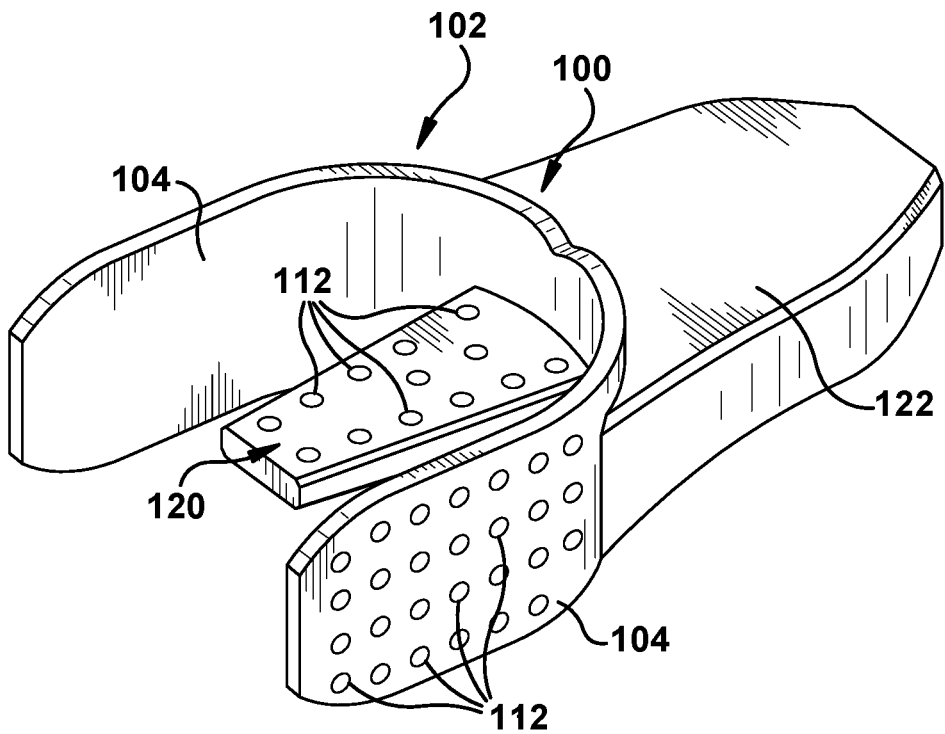
FIG. 15 is a schematic diagram of the intraoral phototherapy device including a central protrusion.
FIG. 16 is a block diagram showing a method for performing phototherapy.

Turning to FIGS. 14 and 15, the phototherapy device 10 may additional include an intraoral component 40 having a contour complimentary to a palate of a user. The intraoral component 40 may rest on the tongue or against the palate when positioned in the oral cavity. For example, the intraoral component 40 may be shaped such that, when positioned in the intraoral cavity, a distance between the intraoral component 40 and a palate and/or tongue of the user does not vary by more than 25 mm. The tissue sensor 30 may also be located on the intraoral component 40. The tissue properties detected by the tissue sensor 30 may include a distance to the target regions 24 and/or a location of the target regions 24. For example, in the occurrence of Oral Mucositis (OM) present in the tonsils or palate (common in HPV-related cancers), the intraoral component (e.g., a mouthpiece accessory) may be used to apply phototherapy to those target areas.

For example, the tissue sensor 30 may detect a distance of tissues located above and/or below the intraoral component 40. The intraoral component 40 may also include light sources 22 located along a top and/or a bottom surface of the intraoral component 40. The circuitry 16 may control the light sources 22 based on a distance between particular light sources and adjacent tissues detected by the tissue sensor 30. For example, as described above, light sources 22 located closer to tissue may have a reduced emission intensity compared to light sources 22 located farther from tissue. In another example, if a tissue (e.g., the tongue) is located close to the sensor 30, then the circuitry 16 may decrease the intensity of light emitted from the intraoral component (e.g., by turning off one or more of the light source(s) supplying the light that is emitted by the intraoral component). Alternatively, if a nearest tissue to the detector is located further from the detector than expected, then the circuitry 16 may increase the intensity of light emitted by the intraoral component 40.

Alternatively or additionally, the intraoral component 40 may include one or more light sources 22 embedded into a portion 74 of the intraoral component located outside the patient's mouth. The intraoral component may comprise a light guide (e.g., made from silicone, acrylic, etc.) configured to transmit light from the one or more light sources to deliver phototherapy to target regions.

In another example, the tissue sensor 30 may detect a location of particular tissues. For example, the tissue sensor 30 may comprise a camera and the camera may distinguish between different tissues in the oral cavity. For example, the circuitry 16 may analyze the images captured by the camera to differentiate between different tissues using image processing techniques. For example, different tissue may be identified based on spectral properties (e.g., color, hue, saturation, intensity, etc.), location (e.g., relative location to other known tissues), shape, etc. As will be understood by one of ordinary skill in the art, the camera may be located inside the intraoral component or located external to the intraoral component (e.g., a camera connected via optics to receive a view of the oral cavity).

Once a tissue of interest has been identified, the circuitry 16 may determine the distance to the particular tissue (e.g., based on the output of the camera or using a separate distance sensor) and modulate the intensity of the light source accordingly. Alternatively or additionally, the circuitry 16 may also steer the light emitted by the intraoral component to focus on the tissue of interest. For example, the light sources 22 of the array of light sources 22 may emit light at different directions. The controller may focus on the tissue of interest by modulating the intensity of light emitted by each of the separate light sources (e.g., by increasing or decreasing power to the separate light sources individually). That is, the circuitry 16 may control the regions illuminated by the illumination source 14, such that the target regions 24 are preferentially illuminated by the illumination source 14. For example, the target regions may be preferentially illuminated by the illumination source such that an optical power of light 28 received by the target regions is at least two, three, or five times higher than an optical power of light 28 received by non-target regions.

As will be understood by one of ordinary skill in the art, the circuitry 16 may steer the emitted light to impact more than one tissue of interest or may be used to avoid particular tissues. For example, the controller may steer the emitted light to avoid the tongue or tissues that are particular susceptible to damage caused by the emitted light.

Figure 13:
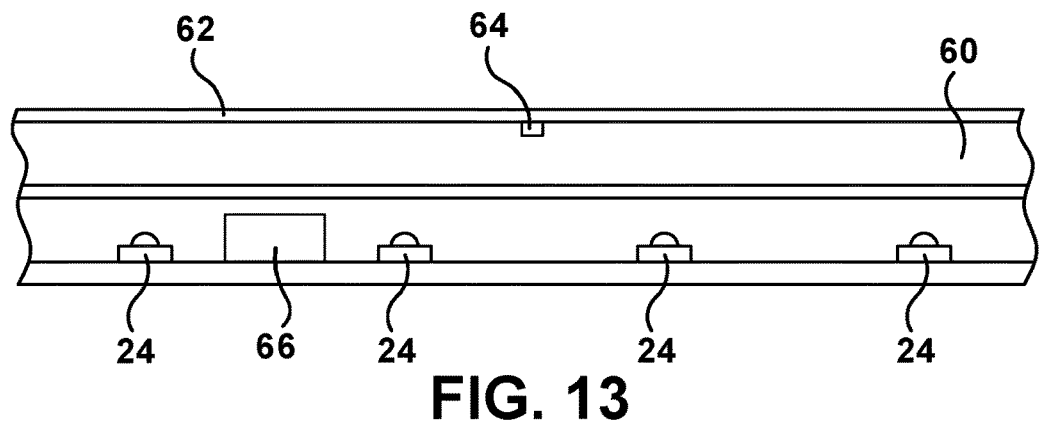
FIG. 13 is a schematic diagram showing a phototherapy device including sensors, a thermal sensor, and light sources.

Turning to FIG. 13, the mask 12 may include a gel 60 positioned between the array of light sources 22 and a contacting surface 62 of the mask 12. The contacting surface contacts 62 the anatomical location when the mask is positioned against the anatomical location. The gel 60 may be a thermal insulator configured to reduce a transfer of heat generated by the illumination source 14 to the contacting surface 62.

The phototherapy device 10 may additional include one or more temperature sensors 64 positioned to detect a temperature of a contacting surface 62 of the mask 12. The contacting surface 62 may contact the anatomical location 18 when the mask is positioned against the anatomical location 18. For example, as shown in FIG. 13, the temperature sensors 64 may be located on the contacting surface 62 of the mask 12. Alternatively, the temperature sensors 64 may be located separate from the contacting surface 62.

The circuitry 16 may be further configured to receive a temperature reading from the temperature sensor 64. The circuitry 16 may reduce the emission of light 28 from the array of light sources 22 when the received temperature reading exceeds a temperature threshold. For example, the circuitry 16 may reduce emission of light 28 by the illumination source 14 so that the array of light sources 22 emits less heat.

The phototherapy device 10 may also include a heatsink for removing heat. The heatsink may passively (e.g., a finned piece of metal) or actively (e.g., using a fan) remove heat generated by the illumination source 14.

Figure 12:
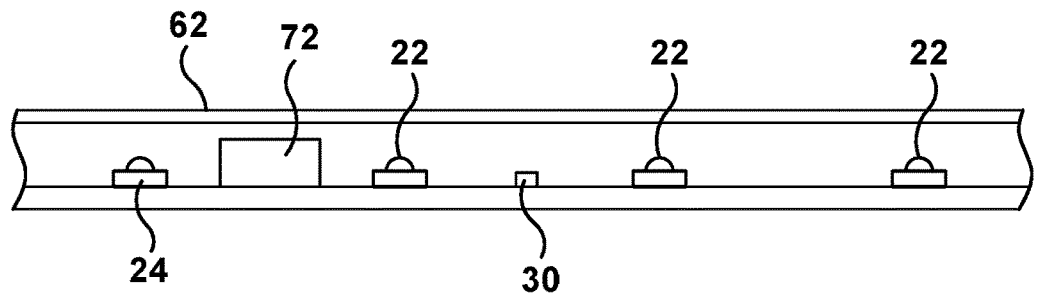
FIG. 12 is a schematic diagram showing a phototherapy device including sensors, an actuator, and light sources.

Turning to FIG. 12, the phototherapy device 10 may additionally include an actuator 72 configured to alter tissue properties to improve penetration to the targeted regions 22 of the light 28 emitted by the illumination source 14. For example, the actuator may emit at least one of vibrations or sound waves. As an example, the circuitry 16 may control the actuator 72 to improve the percentage of light emitted by the illumination source 14 that reaches the target regions 24.

The phototherapy device 10 may additional include one or more safety sensors 66 configured to detect when the mask 12 is positioned adjacent the anatomical location 18. The circuitry may be configured to receive from the safety sensors 66 a signal indicating whether the mask is positioned adjacent the anatomical location 18. When the signal indicates that the mask 12 is not positioned adjacent the anatomical location 18, the circuitry 16 may prevent the illumination source 12 from emitting light 28. For example, the safety sensor 66 may comprise a distance sensor configured to detect a distance to an adjacent surface (e.g., an ultrasonic distance sensor, a photodetector, etc.). In this way, the phototherapy device 10 may reduce the risk of the emitted light 28 damaging a user's eyes, by preventing the illumination source 16 from emitting light 28 when the mask 12 is not positioned adjacent another surface.

The mask 12 may additionally include eye shields to protect the user's eyes from damage caused by light emitted by the illumination source 14.

The phototherapy device 10 may additionally include a power source 82. The power source 82 may comprise a battery and/or a plug for connecting to an external source of electricity (e.g., an electrical outlet). For example, the phototherapy device 10 may include a battery 82 configured to provide electrical power to at least one the illumination source 14 or the circuitry 16.

The phototherapy device 10 may be operated by the patient, eliminating the need for a trained technician. The mask may be custom-made to match the patient's unique facial geometries. An initial therapy session may have a physician perform any necessary adjustments to the mask and explain to the patient how to operate the device. Subsequent therapy sessions may be performed solely by the patient by placing the mask around their face by connecting straps that wrap around the backside of the patient's head and starting the device. To reduce the risk of operating the device without the mask being properly aligned, the device may include a controller configured to detect if skin is contacting the mask at key locations on the mask.

In FIG. 14 an intraoral phototherapy device 100 for directing light onto an oral cavity of a patient is shown. The intraoral phototherapy device 100 includes a main body 102 shaped to conform to contours of the oral cavity when inserted therein. The main body includes a pair of laterally spaced side wings 104 sized and shaped to be received between a patient's teeth and cheeks on opposite sides of the oral cavity.

The intraoral phototherapy device 100 also includes an illumination source 110 comprising a plurality of micro-light emitting diodes (LEDs) 112 positioned on the main body 102 such that light emitted by the micro-LEDs 112 is directed to targeted regions of the oral cavity when the main body is positioned in the oral cavity. The targeted regions of the oral cavity include the mandibular and maxillary buccal surfaces.

The main body 102 may additionally include a central protrusion 120 intermediate the side wings 104 that directs the light to particular targeted regions of the oral cavity. The particular targeted regions of the oral cavity additionally include at least one of a tongue, tonsils, and palate. The main body 102 may additionally include a battery 122 configured to supply electrical power to the illumination source 110.

Turning to FIG. 16, a method 200 of preventing oral mucositis is shown. In process block 202, target regions of a user's oral cavity are irradiated with light prior to symptoms of oral mucositis symptoms are found. The target regions include at least one of buccal tissues, tongue tissues, palate tissues, or tonsillar tissues.

It should be appreciated that many of the elements discussed in this specification may be implemented in a hardware circuit(s), a processor executing software code or instructions which are encoded within computer readable media accessible to the processor, or a combination of a hardware circuit(s) and a processor or control block of an integrated circuit executing machine readable code encoded within a computer readable media. As such, the term circuit, module, server, application, or other equivalent description of an element as used throughout this specification is, unless otherwise indicated, intended to encompass a hardware circuit (whether discrete elements or an integrated circuit block), a processor or control block executing code encoded in a computer readable media, or a combination of a hardware circuit(s) and a processor and/or control block executing such code.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A phototherapy device for modulating an optical dosage delivered to tissues within an oral cavity based on an output from a tissue sensor, the phototherapy device comprising:
   a mask shaped to conform to an anatomical location external to the oral cavity when placed against the anatomical location, wherein the anatomical location comprises an area under a chin;
   an illumination source comprising an array of light sources configured to emit light external to the oral cavity to illuminate sub-surface target regions within the oral cavity when the mask is placed against the anatomical location; and
   circuitry configured to:
      receive from the tissue sensor tissue properties, wherein the received tissue properties affect delivery of light to the sub-surface target regions within the oral cavity; and
      based on the received tissue properties, modulate a property of light emitted by the array of light sources and directed towards the sub-surface target regions, such that the sub-surface targeted regions each receive a particular dose of optical power.

2. The phototherapy device of claim 1, wherein the property of light includes at least one of: an intensity, a wavelength, a duration of emission, a coherence, time modulation of emission, or a distance of emission from the target regions.

3. The phototherapy device of claim 2, wherein:
   when the tissue properties indicate decreased attenuation of light prior to reaching the target regions compared to a threshold, the circuitry is configured to affect the light emitted by the array of light sources in the target regions by at least one of:
   decreasing the intensity, decreasing the coherence, decreasing the wavelength, decreasing the duration of emission, altering the time modulation of the emission such that total emission time is decreased, or increasing the distance of emission from the target regions; and when the tissue properties indicate increased attenuation of light prior to reaching the target regions compared to the threshold, the circuitry is configured to affect the light emitted by the array of light sources in the target regions by at least one of:

increasing the intensity, increasing the coherence, increasing the wavelength, increasing the duration of emission, altering a time modulation of the emission such that the total emission time is increased, or decreasing the distance of emission from the target regions.

4. The phototherapy device of claim 2, wherein:

when the distance to the target regions received from the tissue sensor is below a minimum distance threshold, the circuitry is configured to affect the light emitted by the array of light sources in the target regions by at least one of:

decreasing the intensity, decreasing the coherence, decreasing the wavelength, decreasing the duration of emission, or altering the time modulation of the emission such that total emission time is decreased; and when the distance to the target regions received from the tissue sensor is above a maximum distance threshold, the circuitry is configured to affect the light emitted by the array of light sources in the target regions by at least one of:

increasing the intensity, increasing the coherence, increasing the wavelength, increasing the duration of emission, or altering the time modulation of the emission such that total emission time is increased.

5. The phototherapy device of claim 1, wherein the particular dose of optical power varies between at least two of the target regions.

6. The phototherapy device of claim 1, wherein the particular dose of optical power for each of the target regions is between 10 milliwatts/cm2 and 150 milliwatts/cm2.

7. The phototherapy device of claim 6, wherein the particular dose of optical power received by each of the target regions does not vary between the target regions by more than 20%.

8. The phototherapy device of claim 1, wherein the target regions include at least one of: a tonsillar region, buccal tissues of an oral cavity, a hard palate, a soft palate, or tissues on or under a tongue.

9. The phototherapy device of claim 1, further comprising the tissue sensor configured to detect the tissue properties.

10. The phototherapy device of claim 1, wherein the tissue sensor detects at least one of a skin pigment, a tissue thickness, or a tissue fluid content.

11. The phototherapy device of claim 1, wherein the tissue sensor comprises at least one of a magnetic resonance imager (MRI), an infrared (IR) sensor, an ultrasound sensor, an OCT sensor, a dielectric sensor, a photodiode, or a camera.

12. The phototherapy device of claim 1, further comprising an intraoral component having a contour complimentary to a palate of a user.

13. The phototherapy device of claim 12, wherein:

the tissue sensor is located on the intraoral component; and the received tissue properties include a distance to the target regions.

14. The phototherapy device of claim 12, wherein: the tissue sensor is located on the intraoral component; the detected tissue properties include a location of the target regions; and the circuitry is configured to:

control the regions illuminated by the illumination source, such that the target regions are preferentially illuminated by the illumination source.

15. The phototherapy device of claim 14, wherein the target regions are preferentially illuminated by the illumination source such that an optical power of light received by the target regions is at least five times higher than an optical power of light received by non-target regions.

16. The phototherapy device of claim 1, wherein the array of light sources comprises a plurality of light emitting diodes (LEDs).

17. The phototherapy device of claim 15, wherein the array of light sources additionally includes one or more lasers.

18. The phototherapy device of claim 1, wherein the array of light sources is located on the mask.

19. The phototherapy device of claim 18, wherein the array of light sources is positioned on the mask such that heat generated by the array of light sources is directed away from the anatomical location when the mask is positioned against the anatomical location.

20. The phototherapy device of claim 18, further comprising:

one or more temperature sensors positioned to detect a temperature of a contacting surface of the mask, wherein:

the contacting surface contacts the anatomical location when the mask is positioned against the anatomical location; and the circuitry is further configured to:

receive a temperature reading from the one or more temperature sensors and reduce the emission of light from the array of light sources when the received temperature reading exceeds a temperature threshold.

21. The phototherapy device of claim 18, wherein:

the mask includes a gel positioned between the array of light sources and a contacting surface of the mask; and the contacting surface contacts the anatomical location when the mask is positioned against the anatomical location.

22. The phototherapy device of claim 21, wherein the gel is a thermal insulator configured to reduce a transfer of heat generated by the illumination source to the contacting surface.

23. The phototherapy device of claim 1, further comprising an actuator configured to alter tissue properties to improve penetration to the received targeted regions of the light emitted by the illumination source.

24. The phototherapy device of claim 23, wherein the actuator emits at least one of vibrations or sound waves.

25. The phototherapy device of claim 1, further comprising one or more safety sensors configured to detect when the mask is positioned adjacent the anatomical location, wherein:

the circuitry is further configured to:

receive from the one or more safety sensors a signal indicating whether the mask is positioned adjacent the anatomical location; and when the signal indicates that the mask is not positioned adjacent the anatomical location, the circuitry prevents the illumination source from emitting light.

26. The phototherapy device of claim 1, further comprising a battery configured to provide electrical power to at least one the illumination source or the circuitry.

27. The phototherapy device of claim 1, wherein the anatomical location includes at least one of a mouth or a neck.

28. The phototherapy device of claim 1, wherein the mask has a softness less than or equal to 50 Shore A durometer.

29. The phototherapy device of claim 28, wherein a wavelength of light emitted by the illumination source is from 600 nm to 1000 nm.

\* \* \* \* \*